United States Patent
Kafrissen et al.

(10) Patent No.: US 6,251,956 B1
(45) Date of Patent: Jun. 26, 2001

(54) COMBINATION PROGESTIN ORAL CONTRACEPTIVE REGIMEN

(75) Inventors: Michael Kafrissen; Haya Taitel, both of Gladstone, NJ (US)

(73) Assignee: Ortho Pharmaceutical Corporation, Raritan, NJ (US)

( * ) Notice: Subject to any disclaimer, the term of this patent is extended or adjusted under 35 U.S.C. 154(b) by 0 days.

(21) Appl. No.: 09/137,401

(22) Filed: Aug. 20, 1998

(51) Int. Cl.[7] .......... A61P 18/18; A61K 31/565; A61K 31/567

(52) U.S. Cl. .......... 514/843; 514/178; 514/182; 514/170

(58) Field of Search .................. 514/170, 178, 514/182, 843

(56) References Cited

U.S. PATENT DOCUMENTS

| | | |
|---|---|---|
| 4,390,531 | 6/1983 | Edgren . |
| 4,616,006 | 10/1986 | Pasquale . |
| 4,921,843 | 5/1990 | Pasquale . |
| 5,280,023 | 1/1994 | Ehrlich . |
| 5,898,032 * | 4/1999 | Hodgen ................ 514/178 |

* cited by examiner

Primary Examiner—Edward J. Webman
(74) Attorney, Agent, or Firm—Kenneth J. Dow

(57) ABSTRACT

An oral contraception regimen which comprises sequentially administering two or more progestational agents exhibiting different effects on the human endometrium in combination with an estrogen. The invention is also directed to an extended use oral contraception regimen comprising the sequential administration of two or more progestational agents in combination with an estrogen.

13 Claims, No Drawings

COMBINATION PROGESTIN ORAL CONTRACEPTIVE REGIMEN

FIELD OF THE INVENTION

The present invention is directed to a combination hormonal regimen for human oral contraception. More particularly, the present invention is directed to an oral contraception regimen which comprises sequentially administering two or more progestational agents exhibiting different effects on the human endometrium in combination with an estrogen. The invention is also directed to an extended use oral contraception regimen comprising the sequential administration of two or more progestational agents in combination with an estrogen.

BACKGROUND OF THE INVENTION

Oral contraception formulations, containing a combination of a progestin and an estrogen, have been known for some time. A number of different regimens for controlling ovulation and conception with these hormones have been developed. Conventional regimens may provide consistent dosage of either an estrogen or progestin or both throughout the period of administration, or they may vary the amount of estrogen or progestin by increasing or decreasing the dosage employed during the period of administration. For instance, U.S. Pat. Nos. 4,616,006 and 4,390,531 disclose triphasic oral contraception regimens wherein the dosage of progestin is varied in three sequences during the 21 day administration period in an effort to minimize side effects and optimize contraceptive activity.

A disadvantage inherent in the current oral contraception regimens is the incidence of abnormal intermenstrual or "breakthrough" bleeding. In general, the intended bleeding pattern with oral contraceptives is usually predictable and occurs during the seven day drug free interval following 21 days of active drug administration. Breakthrough bleeding refers to incidences of bleeding or spotting during the 21 day administration period. Breakthrough bleeding or spotting is reported to occur in about 20–30% of women. The incidence of breakthrough bleeding is the highest during the first few months of treatment and appears to be related to the dose and nature of the hormonal components as well as idiosyncratic responses. Another related problem with conventional oral contraceptive regimens is the occurrence of early withdrawal flow which is any bleeding or spotting during the drug administration interval which continues without interruption into the period wherein drug administration is withdrawn. Since discontinuation of a method of contraception because of abnormal intermenstrual bleeding continues to be an important factor leading to drug discontinuation and unintended pregnancy, there is a need for combined oral contraceptive formulations that meet the various clinical demands of the user and which provide the most acceptable pattern of bleeding.

Extended use regimens have been investigated wherein oral contraceptives are administered for up to three months between cycles. A three month trial of a regimen of oral contraceptives that reduces the frequency of menstruation was first described by Loudon, NB, Br.Med.J. 1977;2:487–90. The advantages of such regimens are that they offer freedom from menstrual flow and premenstrual symptoms for extended periods of time and are generally easier to follow. Such extended use regimens may also have therapeutic use in dysmenorrhea, menorrhagia, premenstrual-type symptoms and menstrual migraine. Sulalc et al., Obstet-Gynecol 1997;89: 179–83 in a restropective analysis, reports that 74% of the patients treated with 6 weeks of continuous active pills were stabilized and that the extended oral contraceptives regimen delayed the onset and severity of reported complaints. However, such extended use regimens are hampered by a high incidence of breakthrough bleeding, which is a common cause for discontinuation of the regimen.

Accordingly, there is a need for an oral contraceptive treatment regimen which reduces the incidence of bleeding abnormalities. As will be seen, there is also a related need for an oral contraceptive treatment regimen which achieves this reduction in the incidence of bleeding abnormalities while exhibiting a favorable effect on endometrial morphology.

There is also a need for an extended use oral contraceptive treatment regimen which achieves effective contraception but which exhibits a reduced incidence of bleeding abnormalities.

Different progestins in combined oral contraceptives appear to be associated with different bleeding patterns. While the mechanism for bleeding irregularities is still poorly understood, applicants have observed different patterns of breakthrough bleeding and spotting in comparative studies of the combination oral contraceptives norgestimate/ethinyl estradiol versus levonorgestrel/ethinyl estradiol. The variation in the bleeding patterns was more pronounced in those patients who were not taking oral contraceptives in the cycles prior to the study. In general, the overall proportions of breakthrough bleeding episodes were similar, but the patterns differed.

Progestational agents also differ in their effects on the endometrium. This can range from a proliferative or secretory endometrium to a non-vascular or atrophic condition which can resemble the postmenopausal histological structure. These effects are manifested by morphological changes in the endometrial glands, spiral capillaries, endometrial stroma and epithelial tissues. Cycle control during oral contraceptive use is related to the pattern of endometrial maturation. Thus, depending on the progestational agent used, one can detect histological differences between preparations which could subsequently influence the bleeding patterns. The endometrial morphology appearance has been observed to be different between norgestimate and levonorgestrel formulations. After six months treatment with norgestimate/ethinyl estradiol, well preserved lining epithelium was observed corresponding to midcycle or early secretory phase of the normal menstrual cycle. (Rabe, T. et al, Gerbutsch Fauenheilk 1986,46:883).

Norgestimate was found to have an endometrial sparing effect in primates in comparison to other progestins. (Wilborn, WH et al, 1984, 4th Annual Meeting of Ala. Academy of Science, Tuscaloosa, Ala.). In general, the findings during treatment in humans with norgestimate containing oral contraceptives indicate a secretory transformation of well developed endometrium which was found however incapable of supporting an implanted blastocyte. In contrast, women treated with levonorgestrel containing oral contraceptives generally exhibit atrophic endometrial appearance with diminished gland diameter and glandular epithelial.

SUMMARY OF THE INVENTION

The present invention relates to a combination progestin and estrogen hormonal method and regimen for human contraception involving the sequential administration of two or more different progestational agents in combination with an estrogen comprising the steps of:

(a) administering a contraceptively effective amount of an endometrial sparing progestin in combination with an estrogen in single daily doses for a period of 7–14 days followed by;

(b) administering a contraceptively effective amount of an atrophizing progestin in combination with an estrogen in single daily doses for a period of 7–14 days;

(c) repeating steps (a) and (b) for a period of 21–90 days;

(d) withdrawing the administration for a period of 6–8 days; and (e) repeating steps (a)–(d) continuously.

In a further embodiment, the invention provides a method of reducing breakthrough bleeding resulting from the administration of an effective ovulation suppressing amount of a combination progestin/estrogen oral contraceptive comprising administering an atrophizing progestin for 7–14 days, followed by administering an endometrial sparing progestin for 7–14 days and repeating this cycle for a period of 21–90 days before withdrawing the oral contraceptive for 6–8 days.

In a further embodiment, the invention relates to a method of reducing bleeding abnormalities in an extended use trimonthly oral contraceptive treatment regimen in accordance with the above regimen wherein the oral contraceptive is administered for a period of about 90 days prior to withdrawal.

Another aspect of the invention relates to a pharmaceutical package in the form of a tablet dispenser containing single daily doses of the combination oral contraceptive designed to administer the above mentioned method.

DETAILED DESCRIPTION

In accordance with the present invention, a combination progestin oral contraceptive regimen is provided which involves alternating an endometrial sparing progestin with an atrophizing progestin at intervals which may alter endometrial morphology thereby reducing breakthrough bleeding by preventing both irregular shedding of atrophied endometrium and the breakdown of very glandular endothelium in the later phases of continuing stimulation. By providing a balance of these two effects in sequential phases, the method may permit prolonged intervals between withdrawal bleeds.

The term "Endometrial Sparing" progestin means any compound which exhibits progestational activity and which induces a secretory endometrial morphology with a well preserved glandular structure. Examples of endometrial sparing progestins are norgestimate and norethindrone.

As used herein, the term "atrophizing progestin" refers to any compound which exhibits progestational activity and which induces an atrophic endometrial morphology with diminished gland diameter and glandular epithelial. Examples of atrophizing progestins are desogestrel, gestodene and levonorgestrel.

As stated, applicants have observed different bleeding patterns associated with different progestins. In a randomized comparative study of norgestimate/ethinyl estradiol (NGM/EE 250/35) versus levonorgestrel/ethinyl estradiol (LNG/EE 150/30), different patterns of breakthrough bleeding and spotting were observed. In general, the overall proportions of bleeding episodes were similar, however, the patterns (i.e. when in the cycle the episode occurred) were different. Thus, by making use of this observation concerning the difference in bleeding patterns and the knowledge of the different endometrial morphology associated with the different progestins, a method of reducing the incidence of breakthrough bleeding is obtained by combining the use of progestins exhibiting these different characteristics in the manner of this invention.

In accordance with the present invention, the combination progestin oral contraceptive composition is administered for a period of 21–90 days. This is followed by a period of 6–8 days in which the hormones are withdrawn to allow normal menstruation. Day one of the cycle is defined as the first day of administration. The days are then numbered sequentially until the hormone is withdrawn and menstruation occurs. A placebo or other hormone-free agent such as an iron supplement may be administered during the withdrawal phase.

The combination progestin contraceptive composition of the present invention comprises 21–90 separate dosage units intended for single daily dosage administration. The composition consists essentially of; a first phase of 7–14 dosage units containing an atrophizing progestin in combination with an estrogen in admixture with a pharmaceutically acceptable carriers; a second phase of 7–14 dosage units containing and endometrial sparing progestin in combination with an estrogen and a pharmaceutically acceptable carrier and, optionally, additional phases of alternating atrophizing progestin and endometrial sparing progestin in combination with an estrogen for a total period of 21–90 days. The composition may optionally contain 6–8 daily dosage units of hormone free units. The dosage and nature of the estrogen component will generally remain constant throughout the cycle while the nature of the progestin is sequentially alternated. The dosage of the progestin in each phase may also be varied as necessary to achieve maximum effect.

Any conventional estrogen may be employed as the estrogenic component of the combination oral contraceptive of the present invention. Preferably, the estrogen component is employed in a daily dosage equivalent to about 0.020–0.050 mg of ethinyl estradiol, preferably about 0.030 mg ethinyl estradiol equivalent.

The progestin component is preferably administered in a daily dosage corresponding in progestational activity to 0.065–2.0 mg norethindrone per day. The dosage of the progestin component may also be varied in biphasic or triphasic sequences so that less progestin is administered in the early stage of administration with increasing dosages utilized in the latter stages of administration. For example, a biphasic dosage may be utilized wherein the dosage of endometrial sparing progestin administered in the first phase of administration may correspond in progestational activity to 0.065–0.75 mg norethindrone per day, while the dosage of atrophizing progestin administered in the second stage may range in progestogenic activity from 0.25–2.0 mg norethindrone per day. Similarly, the dosage of progestin may be adjusted in a triphasic manner as disclosed in U.S. Pat. Nos. 4,616,006 and 4,390,531. It may also be desirable to administer the estrogen component alone for the first 1–7 days of administration following the onset of menses as disclosed in U.S. Pat. Nos. 4,921,843 and 5,280,023.

The combination progestin regimen of the present invention is particularly useful for trimonthly extended use continuous therapy wherein the hormones are administered continuously for a period of up to three months before administration is withdrawn and withdrawal bleeding occurs. It is contemplated that such a regimen would involve alternating the administration of the endometrial sparing progestin with the atrophizing progestin during the three month period of administration. For example, the endometrial sparing progestin/estrogen combination would be administered for a period of about 7–14 days followed by administration of the atrophizing progestin/estrogen combination for a period of about 7–14 days. The two progestin/estrogen combinations would then be alternated in sequence for the three month extended use period of administration followed by a one week withdrawal flow interval. By alternating the use of the two progestins having differing effects on the endometrium, it is contemplated that the incidence of intermenstrual bleeding would be reduced allowing for the use of the extended regimen with a minimum of adverse effects.

The described dosages are generally preferred, but, of course, may be adjusted to provide the optimal therapeutic response depending upon the requirements of the patient, the weight and age of the patient, the particular hormone combination composition employed and the relative potency of the drugs involved. The determination of optimum dosages for a particular situation is within the skill of the medical arts.

In accordance with the present invention, the estrogen and progestin agents are preferably administered together orally in association with a pharmaceutically acceptable carrier. In general, the active agents may be combined with one or more pharmaceutically acceptable carriers, for example, solvents, diluents and the like, and may be administered orally in such forms as tablets, capsules, dispersible powders, granules or suspensions containing, for example, from about 0.05 to 5% of suspending agent, syrups containing, for example, from about 10 to about 50% of sugar, and elixirs containing, for example from about 20 to 50% ethanol, and the like, together with the usual additives or vehicles, in accordance with generally acceptable pharmaceutical practice. Such pharmaceutical preparations may contain, for example, from about 0.05 up to about 90% of the active ingredient in combination with the carrier, more usually between about 5% and 60% by weight. While the estrogen and progestin components are preferably combined for oral administration, the estrogen and progestin components may be administered separately or parenterally.

The carrier may be one or more substances which act as diluents, flavoring agents, solubilizers, lubricants, suspending agents, binders or tablet disintegrating agents as well as encapsulating materials. Suitable solid carriers include starch, lactose, dicalcium phosphate, microcrystalline cellulose, sucrose, talc, magnesium carbonate, kaolin and the like. Suitable liquid carriers include sterile water, polyethylene glycol, non-ionic surfactants and edible oils such as peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents and antioxidant agents, for example, vitamin E, ascorbic acid, BHT and BHA.

The active agents may also administered by other art recognized means as practiced in the pharmaceutical arts. For example, the estrogen and progestin alone or in combination may be formulated for administration transdermally via a skin patch, by intramuscular injection, contained within an inert matrix which is implanted within the body and in a depot state, or intravaginally in a matrix that slowly releases the active compositions.

The active compounds may also be administered parenterally. Solutions or suspensions of the active components can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical compositions are preferably packaged in the form of a pharmaceutical kit or package in which the daily dosages are arranged for proper sequential administration. This invention also relates, therefore, to a pharmaceutical package which contains the combination estrogen and progestin active agents in individual dosage units in a synchronized, fixed sequence, wherein the sequence corresponds to the oral contraceptive regimen of the present invention.

For example, the pharmaceutical package can be in the form of a kit containing individual tablets arranged sequentially and consisting of 7–14 single daily doses of the endometrial sparing progestin in combination with the estrogen, followed by 7–14 single daily doses of the atrophizing progestin in combination with the estrogen. This sequence of tablets may be alternated for a total of 21–90 tablets. Finally, the active agent containing tablets may be optionally followed with up to seven placebo tablets so that a tablet may be administered each day continuously.

The method of the present invention can be further understood by the following examples, but should not constitute a limitation thereof.

EXAMPLE 1

Uniphasic Dosage Regimen

On days 1–10 inclusive, 0.035 mg of ethinyl estradiol with 0.250 mg of norgestimate is administered daily. From Day 11–21, inclusive, 0.035 mg of ethinyl estradiol with 0.150 mg levonorgestrel is administered daily. From days 22–28, inclusive, a placebo is administered during which time menstruation occurs. This regimen is illustrated in Table I.

TABLE I

| Day | Estrogen | Progestin |
| --- | --- | --- |
| 1–10 | 0.035 mg EE | 0.250 mg NGM |
| 11–21 | 0.035 mg EE | 0.150 LNG |
| 22–28 | Placebo | |

EE = Ethinyl Estradiol
NGM = Norgestimate
LNG = Levonorgestrel

EXAMPLE 2

Biphasic Dosage Regimen

A Biphasic Dosage regimen is utilized in accordance with the regimen set forth in the following Table II.

TABLE II

| Day | Estrogen | Progestin |
| --- | --- | --- |
| 1–10 | 0.035 mg EE | 0.180 mg NGM |
| 10–21 | 0.035 mg EE | 0.150 mg LNG |
| 21–28 | Placebo | |

EXAMPLE 3

Triphasic Dosage Regimen

A Triphasic dosage regimen is utilized in accordance with the regimen set forth in the following Table III.

TABLE III

| Day | Estrogen | Progestin |
| --- | --- | --- |
| 1–7 | 0.035 mg EE | 0.180 mg NGM |
| 8–14 | 0.035 mg EE | 0.215 mg NGM |
| 15–21 | 0.035 mg EE | 0.150 mg LNG |
| 21–28 | Placebo | |

EXAMPLE 4

Trimonthly Extended Use Regimen

A trimonthly extended use regimen is utilized in accordance with the regimen set forth in the following Table IV.

TABLE IV

| Day | Estrogen | Progestin |
| --- | --- | --- |
| 1–14 | 0.035 mg EE | 0.250 mg NGM |
| 15–28 | 0.035 mg EE | 0.150 LNG |
| 29–43 | 0.035 mg EE | 0.250 mg NGM |
| 44–57 | 0.035 mg EE | 0.150 mg LNG |
| 58–71 | 0.035 mg EE | 0.250 mg NGM |
| 72–83 | 0.035 mg EE | 0.150 mg LNG |
| 84–90 | placebo | |

What is claimed is:

1. A combination progestin and estrogen hormonal method for human contraception involving the sequential administration of two or more different progestational agents in combination with an estrogen comprising the steps of:
   (a) administering a contraceptively effective amount of an endometrial sparing progestin in combination with an estrogen in single daily doses for a period of 7–14 days followed by;
   (b) administering a contraceptively effective amount of an atrophizing progestin in combination with an estrogen in single daily doses for a period of 7–14 days;
   (c) repeating steps (a) and (b) for a period of 21–90 days;
   (d) withdrawing the administration for a period of about seven days; and
   (e) repeating steps (a)–(d) continuously.

2. The method in accordance with claim 1 wherein the endometrial sparing progestin is selected from the group consisting of norgestimate and norethindrone; the atrophizing progestin is selected from the group consisting of desogestrel, gestodene and levonorgestrel; and the estrogen is selected from the group consisting of ethinyl estradiol, mestranol, and 17-beta-estradiol.

3. The method in accordance with claim 2 wherein the endometrial sparing progestin is norgestimate.

4. The method in accordance with claim 2 wherein the atrophizing progestin is levonorgestrel.

5. The method in accordance with claim 2 wherein the atrophizing progestin is desogestrel.

6. The method according to claim 1 wherein the endometrial sparing progestin is norethindrone in a dosage range of about 0.065–2.0 mg per day; the atrophizing progestin is levonorgestrel in a dosage range of 0.050–0.250 mg per day; and the estrogen is ethinyl estradiol in a dosage range of about 0.020–0.050 mg per day.

7. The method of claim 1 wherein the method comprises:
   a) administering a contraceptively effective amount of a endometrial sparing progestin in single daily doses for 10 days;
   b) administering a contraceptively effective amount of an atrophizing progestin in single daily doses for 11 days;
   c) withdrawing administration for seven days; and
   d) repeating steps a)-c) continuously.

8. An extended use combination progestin and estrogen hormonal method for human contraception involving the sequential administration of two or more different progestational agents in combination with an estrogen comprising the steps of:
   (a) administering a contraceptively effective amount of an endometrial sparing progestin in combination with an estrogen in single daily doses for a period of 7–14 days, followed by;
   (b) administering a contraceptively effective amount of an atrophizing progestin in combination with an estrogen in single daily doses for a period of 7–14 days;
   (c) repeating steps (a) and (b) for a period of 90 days;
   (d) withdrawing the administration for a period of about seven days; and
   (e) repeating steps (a)–(d) continuously.

9. The method in accordance with claim 8 wherein the endometrial sparing progestin is norethindrone in a dosage range of about 0.065–2.0mg per day; the atrophizing progestin is levonorgestrel in a dosage range of 0.050–0.250 mg per day; and the estrogen is estradiol in a dosage range of about 0.020–0.050 mg per day.

10. A combination progestin and estrogen hormonal method in accordance with claim 1 wherein the dosage of the estrogenic component is constant throughout the administration period and the relative dosages of the progestin components are constant throughout the administration period.

11. A combination progestin and estrogen hormonal method in accordance with claim 10 wherein 0.035 mg of ethinyl estradiol is administered daily on days 1–21; 0.250 mg of norgestimate is administered daily on days 1–10; and 0.150 mg levonorgestrol is administered daily on days 11–21.

12. A combination progestin and estrogen hormonal method in accordance with claim 1 wherein the dosage of estrogenic component is constant throughout the administration period but the relative dosage of the progestin components are increased in a biphasic manner such that the relative dosage of the atrophizing progestin administered in step (b) is greater than the dosage of the endometrial sparing progestin administered in step (a).

13. A biphasic combination progestin and estrogen hormonal method in accordance with claim 12 wherein 0.035 mg of ethinyl estradiol is administered daily on days 1–21; 0.180 mg of norgestimate is administered daily on days 1–10; and 0.150 mg levonorgestrel is administered daily on days 11–21.

* * * * *